(12) United States Patent
Parton et al.

(10) Patent No.: US 8,426,619 B2
(45) Date of Patent: Apr. 23, 2013

(54) CONTINUOUS PRODUCTION OF FURFURAL AND LEVULININC ACID

(75) Inventors: Rudy Francois Maria Jozef Parton, Echt (NL); Marinus Petrus Wihelmus Maria Rijkers, Echt (NL); Johannes Augustinus Kroon, Echt (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/529,352

(22) Filed: Jun. 21, 2012

(65) Prior Publication Data

US 2012/0330040 A1    Dec. 27, 2012

(30) Foreign Application Priority Data

Jun. 22, 2011 (EP) .................................... 11171003

(51) Int. Cl.
*C07D 307/50* (2006.01)
(52) U.S. Cl.
USPC .......................................................... 549/489
(58) Field of Classification Search .................. 549/489
See application file for complete search history.

(56) References Cited

U.S. PATENT DOCUMENTS

| 4,897,497 A | 1/1990 | Fitzpatrick |
| 5,608,105 A | 3/1997 | Fitzpatrick |
| 7,520,905 B1 | 4/2009 | Lightner |

FOREIGN PATENT DOCUMENTS

| WO | 03/074781 | 9/2003 |
| WO | 2010/030617 | 3/2010 |

OTHER PUBLICATIONS

Extended European Search Report for EP-111710034.4 Completed Oct. 18, 2011.
Mascal et al., "Towards the Efficient, Total Glycan Utilization of Biomass," ChemSusChem, vol. 2, No. 5, pp. 426-426 (2009).

*Primary Examiner* — Taofiq A Solola
(74) *Attorney, Agent, or Firm* — Baker Donelson Bearman Caldwell & Berkowitz

(57) ABSTRACT

A process for continuously producing furfural and levulinic acid from biomass, said process comprising steps including pre-treatment of the biomass; hydrolysis and dehydration of the biomass; removing a vapor mixture by flashing the slurried biomass and a heat integration step comprising the water used being heated through a heat exchange system with the flashed vapor mixture.

9 Claims, 1 Drawing Sheet

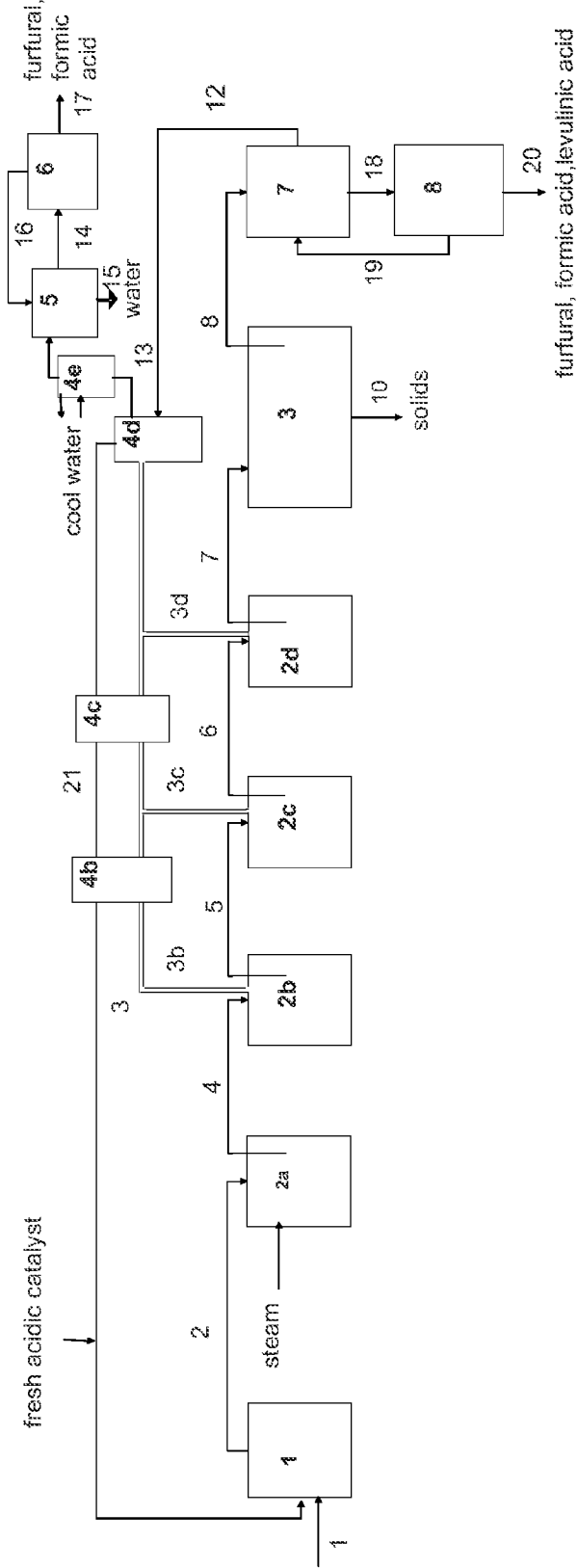

CONTINUOUS PRODUCTION OF FURFURAL AND LEVULININC ACID

CROSS REFERENCE TO RELATED APPLICATIONS

This application claims priority to European Application No. 11171003.4. filed Jun. 22, 2011, the content of which is incorporated herein by reference in its entirety.

BACKGROUND OF THE INVENTION

1. Field of the Invention

This invention relates to the continuous production of furfural and levulinic acid with a heat integration step.

2. Description of Related Art

The needs of the developed work are currently dependent on the utilisation of fossil fuels to produce industrial chemicals and liquid fuels. The majority of modern synthetic products are thus produced from oil. Concerns over high fuel prices, security of energy, global climate change and opportunities for rural economic development pushed governments and industries to develop what is known as first generation technologies for producing biofuels from for example maize. However due to the only marginal improvement of the effect on the climate change and the competition with food, a second generation technology was developed based on the more abundant lignocellulosic feedstocks. Many of the high potential energy crops require less energy for their production as well as less fertilizers, they result in minimal soil erosion, often increase the soil carbon content and require less water.

Lignocellulosic feedstocks are typically composed of 35 to 55% cellulose, 15 to 35% hemicellulose and 15 to 35% lignin. Lignocellulosic feedstocks can be used to produce biofuels, such as ethanol, but it is also possible to produce other chemicals. Most of the chemicals produced in both first and second generation technology are the result of fermentations. Contrary to fermentation of starch, the hydrolysis of cellulose is much more difficult and long fermentation times are needed, Often pretreatments are needed to make the cellulose accessible. M. Galbe and G. Zacchi, Appl. Microbiol. Biotechnol., (2002), 59, 618-628 and/or C. N. Hamelinck, G. van Hoojdonck, A. P. C. Faaj, Biomass and Bioenergy, (2005), 28, 384-41.0. However there are processes such as The Biofine process D. J. S. Fitzpatrick, M. H. B. Hayes, Ross, The Biofine Process—Production of levulinic Acid. Furfural, and Formic Acid from Lignocellulosic Feedstocks, "Biorefineries—Industrial Processes and Products, Volume 1, Ed. B. Kamm, P. R. Gruber, M. Kamm, Wiley-VCR, 2006, 139-163 which by contrast are entirely chemical and rely on acid catalysis and allow a wide range of lignocellulosic feedstocks to be used.

When subjecting lignocellulosic feedstock to acid treatment, the hemicellulose hydrolyses relatively easily to C5 and C6 monomers (pentose & hexose) and cellulose will hydrolyse more slowly. Depending on the source of hemicellulose it can contain acetate groups as well, which are hydrolysed to acetic acid. The lignin itself is not hydrolysed. The pentose monomers, upon farther acid treatment, can degrade to furfural, and the cellulose can hydrolyze to glucose and can farther degrade to hydroxymethylfurfural. Hydroxymethylfurfural can degrade still further in the presence of acid to levulinic acid and formic acid. Lignin together with degraded and oligomerised sugar products will end up as char and potentially as tar.

Char can be used as fertiliser or as fuel pellets. Furfural is used as a chemical or as a solvent. Formic acid and acetic acid can be used as chemicals, Levulinic acid can be used to make resins, plasticizers, chemicals, specialty chemicals, herbicides and a fuel extender, methyltetrahydrofuran.

Many plants comprising lignocellulosic materials require a lower level of water to grow and give high yields compared to food crops. Examples are grasses such as miscanthus and switch grass and wood such as poplar and willow, moreover they all have considerable amounts of cellulose and hemicellulose.

Many common waste materials include cellulose or starch. For example, primary sludges from paper manufacture, waste paper, waste wood (e.g. sawdust), as well as agricultural residues such as corn husks, corn cobs, corn stalks, rice hulls, straw and bagasse include high percentages of cellulose. Starch can be found in food processing waste derived, for example, from corn, wheat oats and barley.

U.S. Pat. No. 5,608,105 discloses a continuous process for producing levulinic acid from carbohydrate-containing materials where a carbohydrate-containing material is supplied continuously to a first reactor and hydrolyzed in the presence of a mineral acid. The hydrolysis produces hydroxymethylfurfural, which in turn is hydrolysed to give levulinic acid.

U.S. Pat. No. 4,897,497 discloses a process for producing furfural and levulinic acid from lignocellulose includes subjecting a sample of lignocellulose to several acid degradations to produce levulinic acid and furfural vapours are continuously collected from the mixture.

WO 2003/074781 discloses a process for producing furfural which utilises reactive evaporation and recycling of spent cooking liquors.

WO 2010/030617 discloses a method of recovering levulinic acid from a mixture of furfural and formic acid.

SUMMARY OF THE INVENTION

The present invention features a process for continuously producing furfural and levulinic acid from biomass, said process comprising steps:

i) pre-treatment of the biomass with a preferred particle size in the range of from 1 mm to 5 cm, more preferably 2 mm to 1 cm and most preferably 2 to 5 mm with water and an acid catalyst at a temperature in the range of from 50 to 240° C., preferably from 90° C. to 240° C., more preferably 95° C. to 170° C. for 2 to 60 minutes to produce a slurried biomass;

ii) hydrolysis and dehydration of the slurried biomass at a preferred temperature in the range of from 120 to 250° C., more preferably 160 to 240° C., and especially 180 to 230° C. for a time preferably in the range of from 8 seconds to 60 minutes and more preferably 8 seconds to 30 minutes to produce at least furfural;

iii) removing a vapour mixture comprising furfural and steam by flashing the slurried biomass from step ii) at a temperature between 140 and 220° C., preferable between 140 and 210° C.;

iv) further hydrolysis and dehydration of the slurried biomass at a temperature in the range from 140 to 220° C., preferably from 140 to 210° C. to produce at least furfural;

v) optionally further removing a vapour mixture comprising furfural, formic acid and steam by flashing the hydrolysed slurried. biomass at a temperature between 120 and 200° C. preferably between 120 and 190° C.;

vi) optional further hydrolysis and dehydration of the slurried biomass at a temperature in the range of from 120 to 200° C., preferably between 120 and 190° C. to produce at least levulinic acid and formic acid;

vii) optionally further removing a vapour mixture comprising furfural, formic acid and steam by flashing the hydrolysed slurried biomass at a temperature between 90 and 180° C., preferably between 100 and 170° C.;

viii) separating out a final liquid comprising levulinic acid from the solids in the remaining slurried biomass;

wherein a) the vapour mixture flashed in step iii) and in optional steps v) and vii) is condensed to a liquid comprising water, furfural, formic acid, acetic acid and or hydroxymethylfurfuraldehyde;

b) at least the resultant furfural and optionally formic acid is recovered from the condensed liquid;

c) water resulting from the separation in step viii) and still containing at least some of the acid catalyst is recycled into step i) preferably after recovery of at least some or all of the resultant furfural and levulinic acid;

d) there is a heat integration step comprising the recycled water c) being heated through a heat exchange system with the vapour mixture flashed in step iii) and in optional steps v) and vii).

BRIEF DESCRIPTION OF THE DRAWING

FIG. 1 is a flow diagram illustrating the steps of a preferred reactor layout for the process of the invention. (1) indicates a pre-treatment reactor (impregnation of biomass with acidic catalyst). (2a) is a first hydrolysis pipe reactor. (2b) is a second hydrolysis reactor. (2c) is a third hydrolysis reactor. (2d) is a fourth hydrolysis reactor. (3) is a solids separator vessel, (4b), (4c), (4d), and (4e) are heat exchangers. (5) is an extraction column. (6) is a distillation section. (7) is an extraction column. (8) is a distillation section,

DETAILED DESCRIPTION OF THE INVENTION

The present invention process includes a heat integration step comprising the recycled water containing at least part of the acid catalyst and which is obtained after removing the solids via a separation technique, being heated through a heat exchange system with the steam flashed in step iii) and in optional steps v) and vii). Surprisingly it has been found that the better the heat integration process is due to the successive flash steps, the less reactor fouling occurs, the less insoluble char is produced and. the more the furfural yield is improved. The improvements can be as high as 5% (relative) compared to the traditional process where only one or at a maximum 2 flash steps and no heat integration are applied.

The levulinic acid is preferably produced in at least 45%, preferably at least 50%, more preferably at least 60%, and most preferably at least 70%, of the theoretical yield based on the approximate hexose (C6 sugars) content of the carbohydrate-containing material. Moreover there is an improvement of the yield on levulinic acid as a consequence of the increasing number of flash steps needed for improved, heat integration as high as 5%.

The furfural is preferably produced in at least 40%, and more preferably at least 50%, of the theoretical yield based on the approximate pentose (C5 sugars) content of the carbohydrate-containing material.

The insoluble char is preferably produced in less than 40%, and more preferably less than 35% and more preferably less than 30% compared to the amount of biomass used, Furthermore because of the additional number of flash steps and the heat integration of the vapours with the returning acidic liquid stream, the process of the invention has a considerable energy saving compared to the prior art and furthermore it is much simpler to operate as it is a looped, fully integrated system.

The acid catalyst used in step i) may be any acid but is preferably selected from the group consisting of HCl and $H_2SO_4$ and mixtures thereof. The acid concentration may vary and is preferably in the range of from 0.05 to 8% of the total biomass slurry after the premixing phase (i). The acid concentration also depends on the type of acid used for example when using HCl the concentration is preferably in the range of from 0.05 to 2%, when using $H_2SO_4$ is preferably in the range of from 0.5 to 8%. The time taken for step i) is preferably in the range of from 2 to 60 minutes.

The temperature at which step ii) is carried out also depends on the acid used. For example when using HCl the temperature of step ii) is preferably below 230 V and more preferably below 200 ° C. and when using sulphuric acid is preferably between 180 V and 230° C. The time also depends on the acid used, for example when using HO the time is from 2 seconds to 3 minutes whereas when using sulphuric acid the time is from 5 seconds to 3 minutes. Step ii) is carried out under pressure however it is in equilibrium with vapour pressure. In step ii) not only furfural is produced but also other reaction intermediates e.g. levoglucosan and reaction products e.g. acetic acid may be produced, which may in turn catalyse the degradation and hydrolysis process itself.

A flash is defined as a release of steam and any reaction products. A flash takes place in a very short space of time, usually seconds or less. The flash temperature ranges may overlap but preferably each successive flash is at a temperature of at least 10° C.; and more preferably at least 20° C. lower than the previous flash. The process of the invention can have any number of flashes but preferably comprises 3 or 4 flashing steps.

Flashed vapour is condensed to a liquid, collected and pumped to a purification system eg be distilled to get out furfural, formic, acetic acid, hydroxymethylfurfuraldehyde (HMF) (especially if more than 2 flashes). The advantage of having several flashing steps is that heat integration can be carried out to a higher level of energy recovery. Surprisingly it was found that furfural, levulinic acid and hydroxymethylfurfuraldehyde yields improve as well and formation of char reduces.

In step iii) the vapour mixture comprising furfural and steam may also contain formic acid.

The vapour mixture flashed in step iii) and in optional steps v) and vii) is preferably condensed to a liquid containing comprising water, furfural, formic acid, acetic acid and or HMF which may be recovered.

The chemicals produced by this process, such as levulinic acid, furfural, formic acid, acetic acid and others of the liquid may be recovered by known separation techniques such as extractions, distillation or other separation techniques or combinations of them.

In step iv) the further hydrolysis and dehydration of the slurried produces not only results in some furfural but may also result in some levulinic acid, formic acid and or hydroxymethylfurfuraldehyde being produced as well.

In the process of the invention the solid by-products are recovered in step viii), preferably by centrifugation or filtration and are then dried. Preferably the solids are dried using a filter press. It has been found that using a filter press the enemy needed to further dry the solids is reduced.

Furthermore the acid catalyst that is used may be recovered from the liquid separated out in step viii) and optionally or partly after removal of the chemicals remaining in the liquid phase such as levulinic acid, furfural, acetic acid, and formic acid and reintroduced into step i).

An example of the equipment that can be used to carry out the process of the invention is illustrated in FIG. 1 and comprised a number of linked reactors. The reactors may in another embodiment be tubes. The process may also utilise plug flow reactors, continuous stirred tank reactors (CSTR) or any combination thereof.

The time taken for the process may vary and depends on the number of flashes and hydrolysis steps employed. The overall reaction time is more or less constant and is dependent on the acid used as catalyst and the temperatures applied. It can be as short as 5 to 30 minutes if HO is used and 10 minutes up to 1 hour if sulphuric acid is used.

FIG. 1 is a flow diagram illustrating the steps of a preferred reactor layout for the process of the invention.

1=pre-treatment reactor (impregnation of biomass with acidic catalyst)
2a=first hydrolysis pipe reactor
2b=second hydrolysis reactor
2c=third hydrolysis reactor
2d=fourth hydrolysis reactor
3=solids separator vessel
4b, 4c, 4d, 4e=heat exchangers
5=extraction column
6=distillation section
7=extraction column
8=distillation section Referring to FIG. 1 an aqueous acidified biomass comprising for example wastepaper fibres, paper sludge, sawdust, ground wood, ground corn, starch solution, or other carbohydrate feedstock in dilute mineral acid (e.g., sulphuric acid or hydrochloric acid) is pumped into reactor (1). In reactor (1) the pre-treatment occurs to produce a slurried biomass impregnated with the acid catalyst. The slurried biomass is transferred to reactor (2a) for a first hydrolysis and dehydration where the carbohydrate material is degraded by the acid to produce at least furfural and is then transferred to reactor (2b) for further hydrolysis and dehydration, Cellulose or starch in the feed degrade to hexose monomers and oligomers. Hemicellulose in the feed degrades to both hexose and pentose monomers and oligomers. The pentose monomers and oligomers are further degraded to furfural and the hexose monomers are further degraded to hydroxymethylfurfural. From reactor (2b) a vapour mixture comprising furfural and steam is removed by flashing the slurried biomass via stream (3b). The slurried biomass is transferred to reactor (2c) and then to (2d), and further hydrolysis and dehydration occurs in each reactor. From reactor (2c) a vapour mixture comprising furfural and steam and optionally formic acid is removed by flashing the slurried biomass via stream (3c). From reactor (2d) a vapour mixture comprising furfural and formic acid and steam is removed by flashing the slurried biomass via stream (3d). Then the aqueous liquid comprising levulinic acid is separated from the solids in the remaining slurried biomass in vessel (3). The solids in vessel (3) are separated out via any separation technique such as centrifugation, filtration, sedimentation or other techniques or combinations of techniques.

The levulinic acid and optionally other products such as furfural, formic acid and acetic acid are separated from the water phase via an extraction column (7) from where the water and acid catalyst are recycled (streams 12 and 21) to reactor (1) via integration with the vapours from streams (3b), (3c) and (3d). The solvent is recovered in the distillation section (8) and recycled (stream 19) into solvent which is recycled (stream 19) to the extraction column (7) and furfural, formic acid and. levulinic acid are also recovered in distillation section (8).

Furthermore the vapour mixture flashed from reactors (2b), (2c) and (2d) is condensed to a liquid in heat exchangers (4b), (4c) and (4d) and any furfural, formic acid, acetic acid and HMF is recovered via extraction column (5) and distillation section (6). This is the heat integration step comprising the returning water, containing the acid catalyst, to reactor (1) via steams (12) and (21), which is heated via heat exchange with vapours flashed from reactors (2b), (2c) and (2d) in the heat exchangers (4b), (4c) and (4d).

The invention claimed is:

1. A process for continuously producing furfural and levulinic acid from biomass, said process comprising:
   i) pre-treating the biomass with water and an acid catalyst at a temperature in the range of from 90° C. to 240° C. to produce a slurried biomass;
   ii) hydrolysis and dehydration of the slurried biomass at a temperature between 160° C. and 240° C. to produce at least furfural;
   iii) removing a vapour mixture comprising furfural and steam by flashing the slurried biomass from step ii) at a temperature from 140° C. to 210° C.;
   iv) further hydrolysis and dehydration of the slurried biomass at a temperature from 140° C. to 210° C.;
   v) optionally further removing a vapour mixture comprising furfural, formic acid and steam by flashing the hydrolysed slurried biomass at a temperature from 120° C. to 190° C.;
   vi) optional further hydrolysis and dehydration of the slurried biomass at a temperature from 120° C. to 190° C. to produce at least levulinic acid and formic acid;
   vii) optionally further removing a vapour mixture comprising furfural, formic acid and steam by flashing the hydrolysed slurried biomass at a temperature from 100° C. to 170° C.;
   viii) separating out a final liquid comprising levulinic acid from the solids in the remaining slurried biomass;
   wherein
   a) the vapour mixture flashed in step iii) and in optional steps v) and vii) is condensed to a liquid comprising water, furfural, formic acid, acetic acid and or hydroxymethylfurfuraldehyde;
   b) at least the resultant furfural and optionally formic acid is recovered from the liquid condensate;
   c) water resulting from the separation in step viii) and still containing at least some of the acid catalyst is recycled into step i) optionally after recovery of at least some or all of the resultant furfural and levulinic acid;
   d) there is a heat integration step comprising the recycled water c) being heated through a heat exchange system with the vapour mixture flashed in step iii) and in optional steps v) and vii).

2. The process according to claim 1, wherein said acid is selected from the group consisting of HCl and $H_2SO_4$ and mixtures thereof.

3. The process according to claim 1, wherein the acid concentration is in the range of from 0.05 to 4%.

4. The process according to claim 1, wherein the time taken for step i) is in the range of from 2 to 60 minutes.

5. The process according to claim 1, wherein each successive flash is at a temperature of at least 10° C. lower than the previous flash.

6. The process according to claim 1, wherein each successive flash is at a temperature of at least 20° C. lower than the previous flash.

7. The process according to claim 1, wherein the acid catalyst is recovered from step viii) and reintroduced into step i).

8. The process according to claim 1, wherein the solids are recovered in step viii) by centrifugation and are then dried.

9. The process according to claim 8, wherein said solids are dried using a filter press.

* * * * *